(12) United States Patent  
Nojima

(10) Patent No.: US 7,526,958 B2  
(45) Date of Patent: May 5, 2009

(54) AUDIOMETER RECEIVER AND AUDIOMETER

(75) Inventor: Yasuo Nojima, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 69 days.

(21) Appl. No.: 11/801,995

(22) Filed: May 11, 2007

(65) Prior Publication Data

US 2007/0261491 A1    Nov. 15, 2007

(30) Foreign Application Priority Data

May 11, 2006    (JP)    ............... 2006-132700

(51) Int. Cl.
*G01N 29/04* (2006.01)
*G01N 29/30* (2006.01)
*H04R 29/00* (2006.01)

(52) U.S. Cl. ............... 73/579; 73/1.82; 73/585; 381/23.1

(58) Field of Classification Search ........... 73/585, 73/1.82, 579; 381/23.1, 60; 600/559
See application file for complete search history.

(56) References Cited

U.S. PATENT DOCUMENTS

| 3,865,982 | A | * | 2/1975 | Feldman et al. | 340/384.5 |
| 4,748,598 | A | * | 5/1988 | Kopke | 367/13 |
| 4,840,066 | A | * | 6/1989 | Botsco et al. | 73/597 |
| 5,357,953 | A | * | 10/1994 | Merrick et al. | 600/331 |
| 6,468,224 | B1 | * | 10/2002 | Foreman et al. | 600/559 |
| 2004/0073134 | A1 | * | 4/2004 | Wasden et al. | 600/559 |
| 2004/0184618 | A1 | * | 9/2004 | Bengtsson | 381/60 |

* cited by examiner

*Primary Examiner*—Hezron Williams  
*Assistant Examiner*—J M Saint Surin  
(74) *Attorney, Agent, or Firm*—Carrier, Blackman & Associates, P.C.; Joseph P. Carrier; William D. Blackman

(57) ABSTRACT

An audiometer having an air-conduction receiver, a bone-conduction receiver, a masking receiver and an audiometer body is provided, in which the air-conduction receiver, the bone-conduction receiver, and the masking receiver are respectively provided with serial ROMs in which identification information and calibration information of each receiver are stored. The audiometer body comprises a misconnection detector for detecting misconnection of each receiver, a calibration period judging mechanism for judging a calibration transition period of each receiver, and a correction amount computer for computing a correction amount of sound pressure based on the information stored in the serial ROMs.

3 Claims, 3 Drawing Sheets

AUDIOMETER RECEIVER AND AUDIOMETER

CROSS-REFERENCE TO RELATED APPLICATIONS

The present application claims priority from Japanese patent application 2006-132700, filed 11 May 2006. The entire disclosure of the referenced priority document is incorporated herein by reference.

BACKGROUND OF THE INVENTION

1. Field of the Invention

The present invention relates to a receiver for an audiometer and an audiometer, which are used in an audiometric test.

2. Description of the Prior Art

A receiver for an audiometer has uneven characteristics and requires calibration when connected to an audiometer.

In a conventional calibration method, it is known that the audiometer and its receiver are regarded as a pair of systems which are not interchangeable, their serial numbers are controlled in pairs, and their calibration information is stored in a memory which is provided in the audiometer. The audiometer outputs calibrated sound pressure from the receiver for the audiometer (hereinafter referred to as "audiometer receiver") by outputting the driving voltage based on the calibration information stored in the memory.

In the case where the audiometer receiver is replaced by a substitute receiver or a new receiver due to failure, the substitute or new audiometer receiver is connected to an audiometer body, wherein the audiometer body is calibrated. The calibration is carried out by a method whereby a qualified person brings calibration jigs into an audiometric test room or the like where the audiometer is installed or by a method of bringing the audiometer into a factory of the audiometer manufacturer.

However, conducting calibration at a medical site becomes a burden to a hospital and a manufacturer because it is difficult to secure the time and place for the calibration. Further, in the case where the audiometer is brought into the manufacturer's factory for the calibration, an audiometric test can not be carried out while the audiometer is taken away from the hospital. In this case, a patient may be forced to change his examination date or the hospital may be required to carry out the audiometric test using a substitute audiometer of which the operation is unfamiliar even to a qualified person. Thus, the calibration at the manufacturer's factory also becomes a burden to the patient and the hospital.

SUMMARY OF THE INVENTION

It is therefore an object of the present invention to provide an improved audiometer receiver and an audiometer with the audiometer receiver which can solve the problems stated above and can output calibrated sound pressure merely by connecting the audiometer receiver to an audiometer body.

In order to attain this object, according to a first aspect of the present invention, an audiometer receiver comprises a receiver adapted to be operatively connected to an audiometer body and a memory means in which calibration information of the audiometer receiver is stored.

According to a second aspect of the present invention, the audiometer receiver according to the first aspect is provided, in which the memory means is a serial ROM.

According to a third aspect of the present invention, an audiometer is provided with the audiometer receiver according to the first aspect or the second aspect.

According to a fourth aspect of the present invention, an audiometer having an audiometer receiver and an audiometer body is provided, in which the audiometer receiver is provided with a serial ROM which stores identification information and calibration information of the audiometer receiver, and the audiometer body is provided with a misconnection detecting means for detecting misconnection of the audiometer receiver, a calibration period judging means for judging a calibration period of the audiometer receiver, and a correction amount computing means for computing a correction amount for the sound pressure based on the information stored in the serial ROM.

BRIEF DESCRIPTION OF THE DRAWINGS

The above and other objects, features and advantages of the present invention will become more apparent from the following description when taken in conjunction with the accompanying drawings.

DETAILED DESCRIPTION OF THE PREFERRED EMBODIMENTS

Figure 1:
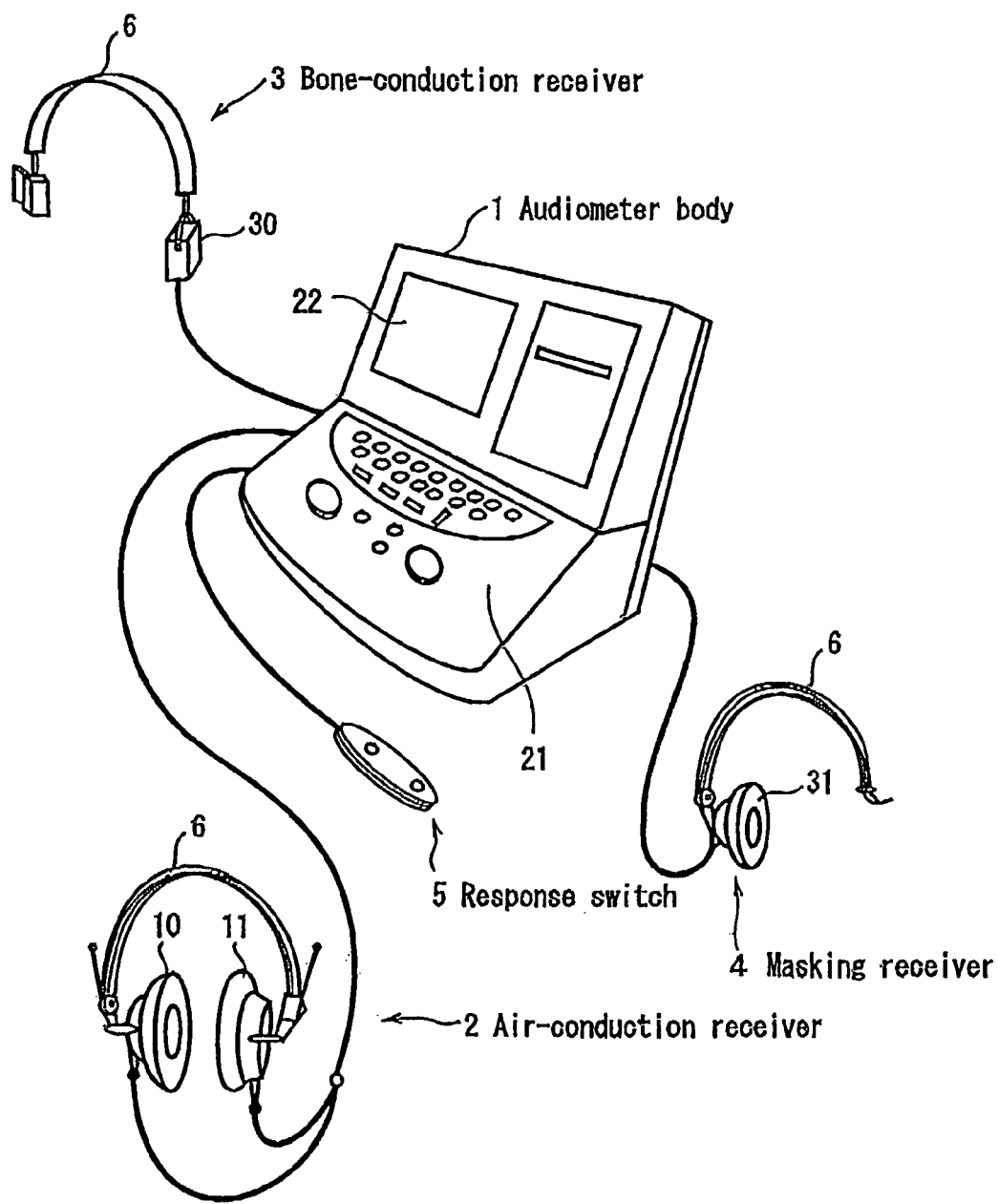
FIG. 1 is a schematic perspective view of an audiometer according to the present invention.

A preferred embodiment of the present invention will now be described with reference to the accompanying drawings. FIG. 1 is a schematic perspective view of an audiometer according to the present invention, FIG. 2 is a schematic diagram of a connector of an audiometer receiver according to the present invention, and FIG. 3 is a block diagram of the audiometer.

As shown in FIG. 1, an audiometer according to the present invention consists of an audiometer body 1, an air-conduction receiver 2, a bone-conduction receiver 3, a masking receiver 4, and a response switch 5. Each receiver 2, 3 and 4 is connected to a headband 6 so that a test subject can wear it during an audiometric test.

Figure 2:
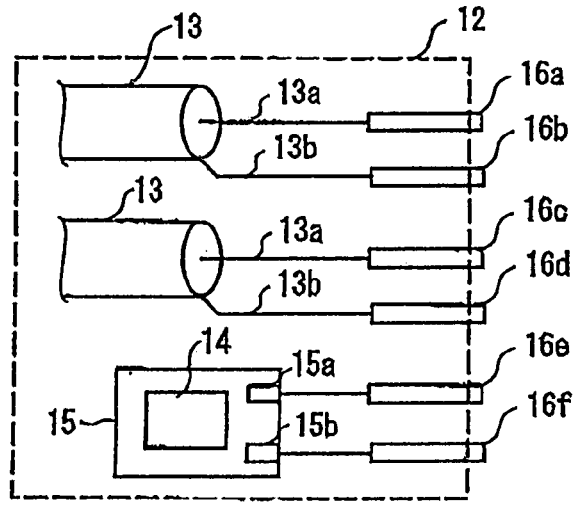
FIG. 2 is a schematic diagram of a connector of an audiometer receiver according to the present invention.
Figure 2:
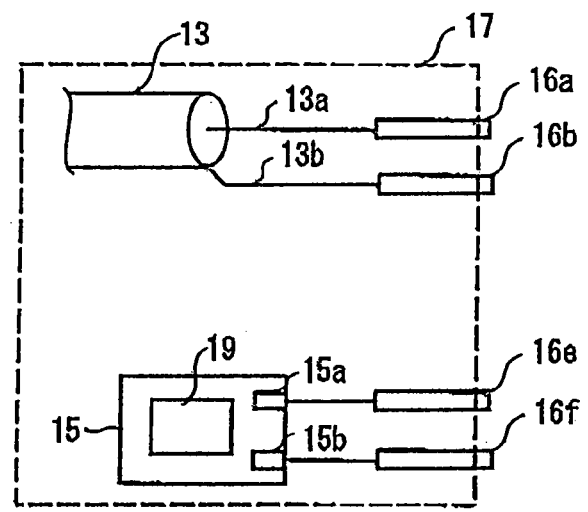
Figure 2:
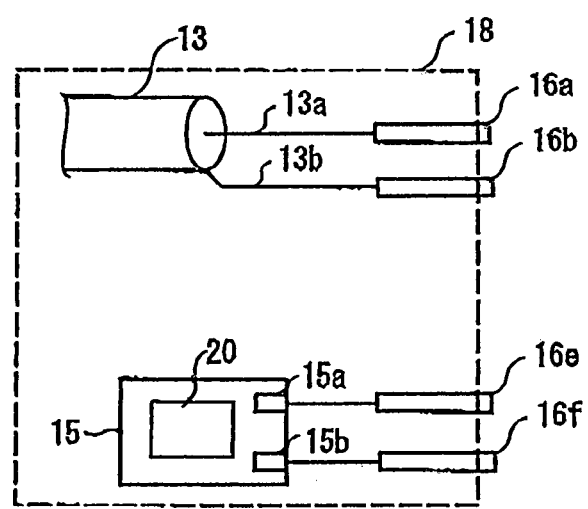
Figure 3:
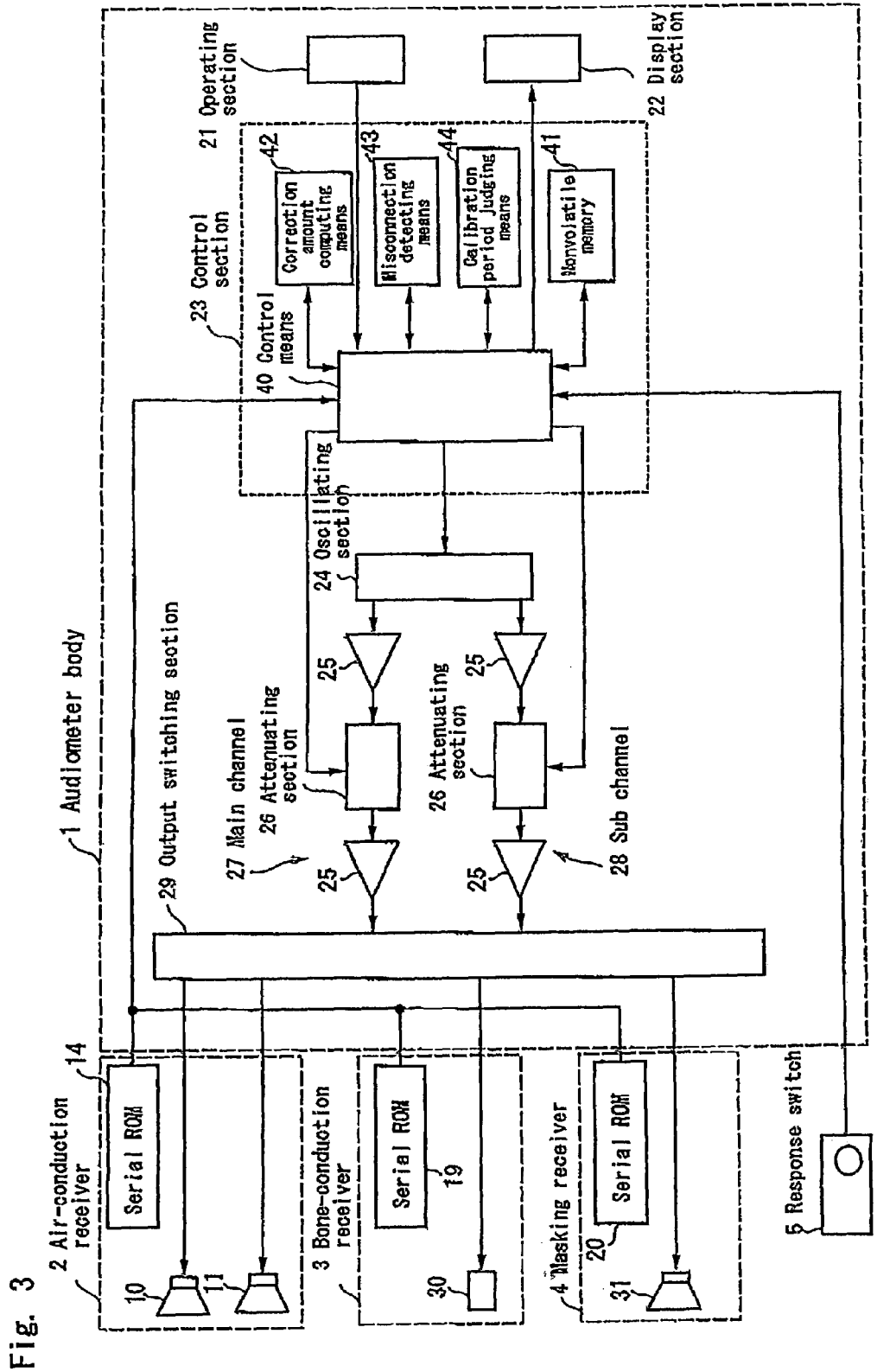
FIG. 3 is a block diagram of the audiometer.

The air conduction receiver 2 is composed, as shown in FIGS. 1 and 2, of a right receiver 10, a left receiver 11, a connector 12 for connecting to the audiometer body 1, and two coaxial cables 13 for connecting the right receiver 10 and the left receiver 11 to the connector 12, respectively. Disposed within the connector 12 is a printed circuit board 15 in which a serial ROM 14 is packaged. Referring to wiring within the connector 12, a core wire 13a and a shielding wire 13b of the coaxial cables 13 are connected to terminal pins 16a, 16b, 16c and 16d, respectively. The serial ROM 14 is arranged so that a signal terminal 15a and a ground terminal 15b are connected to terminal pins 16e and 16f, respectively. It is to be noted that the signal terminal 15a can be connected to an antenna, which can be disposed within the connector 12, to cause the serial ROM to communicate with the audiometer body 1 by wireless.

Data stored in the serial ROM 14 is composed of, for example, a Transducer Electronic Data Sheet (TEDS) structure. The basic TEDS is recorded in the first 64 bits, and the last calibration date and the calibration information are recorded after 256 bits. The serial ROM with capacity of about 1 k bits will do because the audiometer is generally enough if the data for eleven (11) kinds of frequencies is available.

As shown in FIG. 2, the bone-conduction receiver 3 is also composed of a receiver 30, a connector 17 for connecting to the audiometer body 1, and one coaxial cable 13 for connecting the receiver 30 to the connector 17. The masking receiver 4 is also composed of a receiver 31, a connector 18 for connecting to the audiometer body 1, and one coaxial cable 13 for connecting the receiver 31 to the connector 18. The packaging and wiring conditions of the serial ROM 19 within the connector 17 of the bone-conduction receiver 3 and the packaging and wiring conditions of the serial ROM 20 within the connector 18 of the masking receiver 4 are the same as in the air-conduction receiver 2.

The audiometer body 1 is composed, as shown in FIGS. 1 and 3, of an operating section 21 for an examiner to adjust (increase or decrease) the sound pressure of an examination sound or a masking sound, a display section 22 for displaying the examination conditions, results and the like, a control section 23 for controlling an overall operation, an oscillating section 24 for generating a signal, an amplifying section 25 for amplifying the signal, an attenuating section 26 for attenuating the signal generated in the oscillating section 24 by a predetermined amount, and an output switching section 29 for switching the output of a main channel 27 and a sub channel 28.

The right receiver 10 and the left receiver 11 of the air-conduction receiver 2, the receiver 30 of the bone-conduction receiver 3, and the receiver 31 of the masking receiver 4 are respectively connected to the output switching section 29 through connectors 12, 17, and 18. The serial ROMs 14, 19 and 20 of each receiver 2, 3, and 4 are connected to the control section 23. The response switch 5 operated by the test subject when the examination sound is audible is also connected to the control section 23.

Provided within the control section 23 are a control means 40, a nonvolatile memory 41, a correction amount computing means 42, a misconnection detecting means 43, and a calibration period judging means 44. The control means 40 plays the role of transmission and reception of the data to and from the nonvolatile memory 41, transfer of the data to and reception of the computed results from the correction amount computing means 42, transfer of the data to and reception of the detected results from the misconnection detecting means 43, and transfer of the data to and reception of the judged results from the calibration period judging means 44. Stored in the nonvolatile memory 41 are a copy of the data such as the last calibration data and the calibration information which are stored in the serial ROMs 14, 19 and 20, and the tables whereby the relationship of the attenuation of the indicated value of an attenuator operating dial of the operating section 21 is determined.

Operation of the audiometer receiver and the audiometer according to the present invention will now be described. First, each receiver 2, 3 and 4 is connected to an audiometer body 1, wherein the audiometer body 1 is calibrated. The serial ROM 14 provided within the connector 12 of the air-conduction receiver 2 stores the data of Table 1 shown. Below. The serial ROM 19 provided within the connector 17 of the bone-conduction receiver 3 stores the data of Table 2 shown below. The serial ROM 20 provided within the connector 18 of the masking receiver 4 stores the following data of Table 3. The data of the tables 1 through 3 is coded for storing.

TABLE 1

Serial ROM 14

| | | A | A |
|---|---|---|---|
| Maker name | | A | A |
| Model Number | | ABC02W | ABC02W |
| Right and left identification | | right | left |
| Version Number | | 01 | 01 |
| Serial Number | | 0011 | 0012 |
| Calibration date | | Jan. 25, 2005 | Jan. 20, 2005 |
| Correction value of each frequency (dB) | 125 Hz | −0.5 | 0 |
| | 250 Hz | −0.5 | 0 |
| | 500 Hz | −1 | 0 |
| | 750 Hz | −1 | −05 |
| | 1000 Hz | −0.5 | 0 |
| | 1500 Hz | −0.5 | 1 |
| | 2000 Hz | −0.5 | 1 |
| | 3000 Hz | 0 | 1.5 |
| | 4000 Hz | 0.5 | 0.5 |
| | 6000 Hz | 0.5 | 0 |
| | 8000 Hz | 1 | −0.5 |

TABLE 2

Serial ROM 19

| | | A |
|---|---|---|
| Maker name | | A |
| Model Number | | DE04 |
| Right and left identification | | none |
| Version Number | | 03 |
| Serial Number | | 0011 |
| Calibration date | | Jul. 05, 2005 |
| Correction value of each frequency (dB) | 125 Hz | none |
| | 250 Hz | −0.5 |
| | 500 Hz | −0.5 |
| | 750 Hz | −0.5 |
| | 1000 Hz | −0.5 |
| | 1500 Hz | 0 |
| | 2000 Hz | −1 |
| | 3000 Hz | −1 |
| | 4000 Hz | 0 |
| | 6000 Hz | 0 |
| | 8000 Hz | −0.5 |

TABLE 3

Serial ROM 20

| | | A |
|---|---|---|
| Maker name | | A |
| Model Number | | ABC06Y |
| Right and left identification | | none |
| Version Number | | 01 |
| Serial Number | | 0031 |
| Calibration date | | Jan. 25, 2005 |
| Correction value of each frequency (dB) | 125 Hz | −0.5 |
| | 250 Hz | 0 |
| | 500 Hz | −1 |
| | 750 Hz | −1 |
| | 1000 Hz | −0.5 |
| | 1500 Hz | −1 |
| | 2000 Hz | −0.5 |
| | 3000 Hz | 0 |
| | 4000 Hz | 0.5 |
| | 6000 Hz | 0.5 |
| | 8000 Hz | 1 |

For example, when a power switch of the audiometer body 1 is ON after connecting a new air-conduction receiver 2 to the audiometer body 1, the data (Table 1) stored in the serial ROM 14 is read into the control section 23.

In the control section 23, the misconnection detecting means 43 first confirms from the name of the receiver whether the connector (plug) 12 of the air-conduction receiver 2 is connected to a correct connector (receptacle) of the audiometer body 1. In the case where the connector (plug) 12 of the air-conduction receiver 2 is connected to a wrong connector (receptacle), an error message is displayed on the display section 22.

Next, by comparing the data stored in the serial ROM 14 with the data stored in the nonvolatile memory 41, it is confirmed from the serial number and the calibration date whether the air-conduction receiver is the same as used before. When the serial number or the calibration date differs, the data stored in the nonvolatile memory 41 is rewritten as a new data (correction value etc. of each frequency). Further, in the case where the calibration period judging means 44 judges that one year has passed from the calibration date stored in the nonvolatile memory 41, a warning message is displayed on the display section 22. The bone-conduction receiver 3 and the masking receiver 4 also operate in the same manner as the air-conduction receiver 2. Then, a correction amount is computed by the correction amount computing means 42 and the correction amount is reproduced with respect to the attenuation of the table within the nonvolatile memory 41. The correction amount is computed by the correction, amount computing means 42, and the table within the nonvolatile memory 41 is reproduced based on this correction amount.

After setting of the receivers 2, 3 and 4 onto the audiometer body 1 is completed, the test subject is asked to wear each receiver 2, 3 and 4 to start the audiometric test. An examiner operates the operating section 21 to change the frequency and sound pressure of a sound output from the receivers 2, 3 and 4. The test subject presses the response switch 5 when the sound is audible. The condition of the response switch 5 is displayed on the display section 22. The examiner changes the frequency and the sound pressure confirming how the test subject responds and measures the hearing threshold level of the test subject.

For example, when a setting is made by the operating section 21 to output the sound of 60 dB at 1 kHz from the right receiver 10 of the air-conduction receiver 2, if the output of the attenuating section 26 is 130 dB at 1 kHz when setting of the attenuating section 26 is 0 dB, the control section 23 can set the attenuating section 26 at −70 dB referring to the table within the nonvolatile memory 41 so that the output of the attenuating section 26 becomes 60 dB. However, if the table of the right receiver 10 is not corrected, it is not certain that the sound of 60 dB is output at 1 kHz from the right receiver 10 because the frequency characteristics are not considered.

In this manner, the correction amount computing means 42 computes the table for outputting the calibrated sound pressure corresponding to the indicated value of the attenuator operating dial of the operating section 21 from the coded correction value of the right receiver 10 stored in the nonvolatile memory 41, wherein the table stored in the nonvolatile memory 41 is rewritten. Since the correction value of the right receiver 10 at 1 kHz is −0.5 dB from Table 1, the correction amount computing means 42 computes the setting of the table as −70.5 dB. If the control section 23 sets the attenuating value of the attenuating section 26 at −70.5 dB referring to the table, the sound of 60 dB at 1 kHz output from the right receiver 10 is calibrated.

Likewise, if the output of the attenuating section 26 is 130 dB at 2 kHz when the setting of the attenuating section 26 is 0 dB, the setting of the attenuating section 26 can be −70.5 dB to output the sound of 60 dB at 2 kHz from the right receiver 10. Referring to the left receiver 11, the receiver 30 of the bone-conduction receiver 3, and the receiver 31 of the masking receiver 4, the attenuating amount of the attenuating section 26 can also be set in the same manner as in the right receiver 10.

EFFECTS OF THE INVENTION

According to the first aspect of the present invention, the calibrated sound pressure can be output merely by connecting the audiometer receiver to the audiometer body because the audiometer receiver is provided with a memory means in which the calibration information is stored. Further, it is neither necessary to carry out the calibration at the medical site nor to send the audiometer back to the manufacturer's factory and as a result, usability can be improved.

According to the second aspect of the present invention, the calibrated sound pressure can be output merely by connecting the audiometer receiver to the audiometer body because the audiometer receiver is provided with a serial ROM in which the calibration information is stored.

According to the third aspect of the present invention, the calibrated sound pressure can be output merely by connecting the audiometer receiver to the audiometer body because the audiometer receiver, provided with a memory means or a serial ROM in which the calibration information is stored, is used. In this manner, the calibration of the audiometer receiver is unnecessary and as a result, maneuverability improves.

According to the fourth aspect of the present invention, the calibrated sound pressure can be output merely by connecting the audiometer receiver to the audiometer body because the audiometer receiver, provided with a serial ROM in which the calibration information is stored, is used. In this manner, the calibration of the audiometer receiver becomes unnecessary and as a result, maneuverability improves. Further, the calibrated sound pressure can be smoothly output from the audiometer receiver by effectively combining the serial ROM with the misconnection detecting means, the calibration period judging means and the correction amount computing means.

INDUSTRIAL APPLICABILITY

According to the present invention, by using an audiometer receiver provided with a serial ROM in which the calibration information is stored, calibrated sound pressure can be output merely by connecting the audiometer receiver to an audiometer body. It is therefore possible to provide an audiometer which does not require calibration of the audiometer receiver and improves the maneuverability.

Although there has been described what is are the present embodiments of the invention, it will be understood by persons skilled in the art that variations and modifications may be made thereto within the scope of the invention as set forth in the appended claims.

What is claimed is:

1. An audiometer having an audiometer receiver and an audiometer body, characterized in that the audiometer receiver comprises a serial ROM in which identification information and calibration information of the audiometer receiver are stored, and the audiometer body comprises a misconnection detecting means for detecting misconnection of the audiometer receiver, a calibration period judging means for judging a calibration period of the audiometer receiver, and a correction amount computing means for computing a correction amount of sound pressure based on the information stored in the serial ROM.

2. An audiometer comprising an audiometer receiver adapted to be operatively connected to an audiometer body and a memory storing calibration information of the audiometer receiver, wherein:
the audiometer receiver comprises:
a serial ROM in which identification information and calibration information of the audiometer receiver are stored; and
the audiometer body comprises:
a misconnection detector which detects misconnection of the audiometer receiver,
a calibration period judging mechanism which judges a calibration period of the audiometer receiver, and
a correction amount computer which computes a correction amount of sound pressure based on the information stored in the serial ROM.

3. The audiometer according to claim 2, wherein the memory is a serial ROM.

* * * * *

UNITED STATES PATENT AND TRADEMARK OFFICE
CERTIFICATE OF CORRECTION

PATENT NO. : 7,526,958 B2
APPLICATION NO. : 11/801995
DATED : May 5, 2009
INVENTOR(S) : Nojima It is certified that error appears in the above-identified patent and that said Letters Patent is hereby corrected as shown below:

<u>Title page</u>:
    In section (57), "ABSTRACT", 2nd line, after "a masking receiver" insert a --,--.

<u>Column 1</u>:
    Line 36, change "is installed or" to --is installed, or--.

<u>Column 2</u>:
    Line 44, change "response switch S." to --response switch 5.--.
    Line 47, change "air conduction" to --air-conduction--.

<u>Column 3</u>:
    Line 21, change "results and the like," to --results, and the like,--.
    Line 62, change "Table 1 shown. Below." to --Table 1 shown below.--.

<u>Column 4</u>:
    Line 12 (in Table 1), change "750 Hz     $-1$    $-05$" to --750Hz    $-1$    $-0.5$--.

<u>Column 5</u>:
    Line 23, change "rection, amount" to --rection amount--.

<u>Column 6</u>:
    Line 13, after "factory" insert a --,--.
    Line 14, after "result" delete the ",".

UNITED STATES PATENT AND TRADEMARK OFFICE
CERTIFICATE OF CORRECTION

PATENT NO. : 7,526,958 B2
APPLICATION NO. : 11/801995
DATED : May 5, 2009
INVENTOR(S) : Nojima It is certified that error appears in the above-identified patent and that said Letters Patent is hereby corrected as shown below:

Column 6 (continued):
    Line 26, change "and as a result, maneuverability" to --and, as a result, maneuverability--.
    Line 34, change "and as a result, maneuverability" to --and, as a result, maneuverability--.
    Line 38, change "judging means and" to --judging means, and--.
    Line 50, change "Although there has been described what is are" to --Although there have been described what are--.

Signed and Sealed this

Twenty-fourth Day of November, 2009

David J. Kappos
*Director of the United States Patent and Trademark Office*